(12) United States Patent
Bardat et al.

(10) Patent No.: US 8,388,954 B2
(45) Date of Patent: Mar. 5, 2013

(54) STABILISING FORMULATION FOR IMMUNOGLOBULIN G COMPOSITIONS IN LIQUID FORM AND IN LYOPHILISED FORM

(75) Inventors: Annie Bardat, Limours (FR); Edith Begin, Les Ulis (FR); Nassirah Khandoudi, Gif sur Yvette (FR); Olivier Just, Marcoussis (FR); Sami Chtourou, Elancourt (FR); Roland Schmitthaeusler, Montigny le Bretonneux (FR)

(73) Assignee: Laboratoire Francais du Fractionnement et des Biotechnologies, Les Ulis (FR)

(*) Notice: Subject to any disclaimer, the term of this patent is extended or adjusted under 35 U.S.C. 154(b) by 617 days.

(21) Appl. No.: 10/552,314

(22) PCT Filed: Apr. 8, 2004

(86) PCT No.: PCT/FR2004/000871
§ 371 (c)(1),
(2), (4) Date: Sep. 5, 2006

(87) PCT Pub. No.: WO2004/091656
PCT Pub. Date: Oct. 28, 2004

(65) Prior Publication Data
US 2007/0036779 A1    Feb. 15, 2007

(30) Foreign Application Priority Data
Apr. 9, 2003  (FR) .................... 03 04388

(51) Int. Cl.
*A61K 39/395* (2006.01)
(52) U.S. Cl. .................. 424/130.1
(58) Field of Classification Search ............ None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,588,585 A | 5/1986 | Mark et al. | |
| 4,597,966 A * | 7/1986 | Zolton et al. ............ | 424/141.1 |
| 4,666,828 A | 5/1987 | Gusella | |
| 4,683,202 A | 7/1987 | Mullis | |
| 4,737,462 A | 4/1988 | Mark et al. | |
| 4,801,531 A | 1/1989 | Frossard | |
| 4,873,316 A | 10/1989 | Meade et al. | |
| 4,879,111 A | 11/1989 | Chong | |
| 4,879,219 A | 11/1989 | Wands et al. | |
| 4,904,584 A | 2/1990 | Shaw | |
| 4,959,314 A | 9/1990 | Mark et al. | |
| 4,965,195 A | 10/1990 | Namen et al. | |
| 5,011,771 A | 4/1991 | Bellet et al. | |
| 5,017,691 A | 5/1991 | Lee et al. | |
| RE33,653 E | 7/1991 | Mark et al. | |
| 5,116,943 A | 5/1992 | Koths et al. | |
| 5,192,659 A | 3/1993 | Simons | |
| 5,272,057 A | 12/1993 | Smulson et al. | |
| 5,281,521 A | 1/1994 | Trojanowski et al. | |
| 5,486,359 A | 1/1996 | Caplan et al. | |
| 5,591,625 A | 1/1997 | Gerson et al. | |
| 5,843,780 A | 12/1998 | Thomson | |
| 5,928,638 A | 7/1999 | Uchida et al. | |
| 5,945,098 A | 8/1999 | Sarno et al. | |
| 5,968,501 A | 10/1999 | Comoglio | |
| 6,090,622 A | 7/2000 | Gearhart et al. | |
| 6,132,708 A | 10/2000 | Grompe | |
| 6,143,292 A | 11/2000 | Slavin | |
| 6,162,427 A | 12/2000 | Baumann et al. | |
| 6,184,035 B1 | 2/2001 | Csete et al. | |
| 6,248,587 B1 | 6/2001 | Rodgers et al. | |
| 6,258,597 B1 | 7/2001 | Bachovchin et al. | |
| 6,267,958 B1 * | 7/2001 | Andya et al. .............. | 424/130.1 |
| 6,280,718 B1 | 8/2001 | Kaufman et al. | |
| 6,326,198 B1 | 12/2001 | Emerson et al. | |
| 6,383,481 B1 | 5/2002 | Ikehara et al. | |

(Continued)

FOREIGN PATENT DOCUMENTS

| | | | |
|---|---|---|---|
| EP | 0196761 A | 10/1986 | |
| EP | 0196761 A2 | 10/1986 | |

(Continued)

OTHER PUBLICATIONS

Mannitol, MSDS, mallinckrodt chemicals, p. 1-7.*
Glycine, MSDS, Mallinckrodt chemicals, p. 1-6.*
Mannitol, MSDS, Mallinckrodt chemicals, p. 1-7, 2008.*
Glycine, MSDS, Mallinckrdt chemicals, p. 1-6, 2008.*
Aiuti et al., J. Exp. Med., 185(1):111-120 (1997).
Alison et al., Nature, 406:257 (2000).
Azizi et al., Proc. Natl. Acad. Sci. USA, 95:3908-3913 (1998).
Bjornson et al., Science, 283:534-537 (1999).
Byrne et al., Proc. Natl. Acad. Sci. USA, 86:5473-5477 (1989).
Eglitis et al., Proc. Natl. Acad. Sci. USA, 94:4080-4085 (1997).
Galimi et al., J. Cell Biol., 127(6 pt 1):1743-1754 (1994).
Gohda et al., J. Clin. Invest., 81:414-419 (1988).
Jackson et al., J. Clin. Invest., 107(11):1395-1402 (2001).

(Continued)

*Primary Examiner* — Yunsoo Kim
(74) *Attorney, Agent, or Firm* — Birch, Stewart, Kolasch & Birch, LLP

(57) ABSTRACT

This invention is related to a stabilizing formulation for immunoglobulins G compositions comprising a sugar alcohol, glycine and a non-ionic detergent, which is suitable for the stabilization of immunoglobulins G compositions in liquid form and in lyophilized form. The invention also relates to an immunoglobulins G composition in liquid form or in lyophilized form comprising said stabilizing formulation.

6 Claims, 1 Drawing Sheet

U.S. PATENT DOCUMENTS

| | | | |
|---|---|---|---|
| 6,436,704 | B1 | 8/2002 | Roberts et al. |
| 6,447,765 | B1 | 9/2002 | Horwitz |
| 6,447,766 | B1 | 9/2002 | Pelus et al. |
| 6,511,958 | B1 | 1/2003 | Atkinson et al. |
| 6,541,623 | B1 | 4/2003 | Ford et al. |
| 2006/0246060 | A1 * | 11/2006 | Nesta .................. 424/141.1 |

FOREIGN PATENT DOCUMENTS

| | | |
|---|---|---|
| EP | 0 264 166 | 4/1988 |
| EP | 0392717 A1 * | 10/1990 |
| EP | 0 550 769 | 7/1993 |
| EP | 0597101 | 5/1994 |
| EP | 1314437 | 5/2003 |
| JP | 61-191622 | 8/1986 |
| JP | 63-088197 | 4/1988 |
| JP | 5-025058 | 2/1993 |
| JP | 9-500894 | 1/1997 |
| JP | 11-510170 | 9/1999 |
| WO | WO 97/04801 A | 2/1997 |
| WO | WO-97/04801 A1 | 2/1997 |
| WO | WO 98/44948 A | 10/1998 |
| WO | WO-98/44948 A2 | 10/1998 |
| WO | WO-02/13860 | 2/2002 |
| WO | WO-02/092632 | 11/2002 |
| WO | WO 03/009817 A | 2/2003 |
| WO | WO-03/009817 A2 | 2/2003 |

OTHER PUBLICATIONS

Janowska-Wieczorek et al., Stem Cells, 19:99-107 (2001).
Kmiecik et al., Blood, 80(10):2454-2457 (1992).
Kollet et al., Blood, 97(10):3283-3291 (2001).
Kollet et al., J. Clin. Invest., 112(2)160-169 (2003).
Krause et al., Cell, 105:369-377 (2001).
Lagasse et al., Nat. Med., 6(11):1229-1234 (2000).
Lotti et al., J. Virol., 76(8):3996-4007 (2002).
Mezey et al., Science, 290:1779-1782 (2000).
Nagasawa et al., Proc. Natl. Acad. Sci. USA, 91:2305-2309 (1994).
Nishino et al., Blood, 85(11):3093-3100 (1995).
Orlic et al., Nature, 410:701-705 (2001).
Pablos et al., Am. J. Pathol., 155(5):1577-1586 (1999).
Peled et al., Science, 283:845-848 (1999).
Petersen et al., Science, 284:1168-1170 (1999).
Resnick et al., Proc. Natl. Acad. Sci. USA, 90:4591-4595 (1993).
Rubin et al., Proc. Natl. Acad. Sci. USA, 88:415-419 (1991).
Shamblott et al., Proc. Natl. Acad. Sci. USA, 95:13726-13731 (1998).
Takai et al., Blood, 89(5):1560-1565 (1997).
Thomson et al., Proc. Natl. Acad. Sci. USA, 92:7844-7848 (1995).
Thomson et al., Science, 282:1145-1147 (1998).
Tomita et al., Circulation, 100[suppl II]:II-247-II-256 (1999).
Wang et al., Am. J. Pathol., 158(2):571-579 (2001).
Weidner et al., J. Cell. Biol., 111:2097-2108 (1990).
Weissman, Cell, 100:157-168 (2000).
Winoto et al., EMBO J., 8(3):729-733 (1989).
Wright et al., J. Exp. Med., 195(9):1145-1154 (2002).
Zanjani et al., Blood, 94(7):2515-2522 (1999).
Zheng et al., Nat. Biotechnol., 18:176-180 (2000).
Steinbuch, M. et al., "Isolement de l'immunoglobuline IgG du plasma humain a l'aide de l'acide caprylique," Rev. Fr. Etud. Clin. Biol., Dec. 1969, vol. 14, No. 10, pp. 1054-1058.
Bleeker, Wim K. et al., "Vasoactive side effects of intravenous immunoglobulin preparations in a rat model and their treatment with recombinant platelet-activating factor acetylhydrolase," *Blood*, Mar. 1, 2000, vol. 95, No. 5, pp. 1856-1861.
Pikal, Michael J., "Freeze-drying of proteins, part II: Formulation selection," *BioPharm*, Oct. 1990, vol. 3, No. 9, pp. 26-30.
Arakawa, Tsutomu et al., "Protein-solvent interactions in pharmaceutical formulations," *Pharmaceutical Research*, 1991, vol. 8, No. 3, pp. 285-291.
Osterberg, Thomas et al., "Development of a freeze-dried albumin-free formulation of recombinant factor VIII SQ," *Pharmaceutical Research*, 1997, vol. 14, No. 7, pp. 892-898.
Guo, Wei et al., "Raman evidence that the lyoprotectant poly(ethylene glycol) does not restore nativity to the heme active site of horseradish peroxidase suspended in organic solvents," Biomacromolecules, 2002, vol. 3, No. 4, pp. 846-849.
Chidwick, K. et al., "Clinical experience with a new solvent detergent-treated intravenous immunoglobulin free of hypotensive effects," *Vox Sanguinis*, 1999, vol. 77, No. 4, pp. 204-209.
Cohn, E. J. et al., "Preparation and properties of serum and plasma proteins. IV. A system for the separation into fractions of the protein and lipoprotein components of biological tissues and fluids," *J. Am. Chem. Soc.*, Mar. 1946, vol. 68, pp. 459-475.
Kistler, P. et al., "Large scale production of human plasma fractions. Eight years experience with the alcohol fractionation procedure of Nitschmann, Kistler and Lergier," *Vox Sang.*, 1962, vol. 7, pp. 414-424.
Fernades, Peter M. et al., "Preparation of a stable intravenous gamma-globulin: Process design and scale-up," *Vox Sang.*, 1980, vol. 39, No. 2, pp. 101-112.
Levine, Howard L. et al., "The use of surface tension measurements in the design of antibody-based product formulations," Journal of Parenteral Science & Technology, 1991, vol. 45, No. 3, pp. 160-165.

* cited by examiner

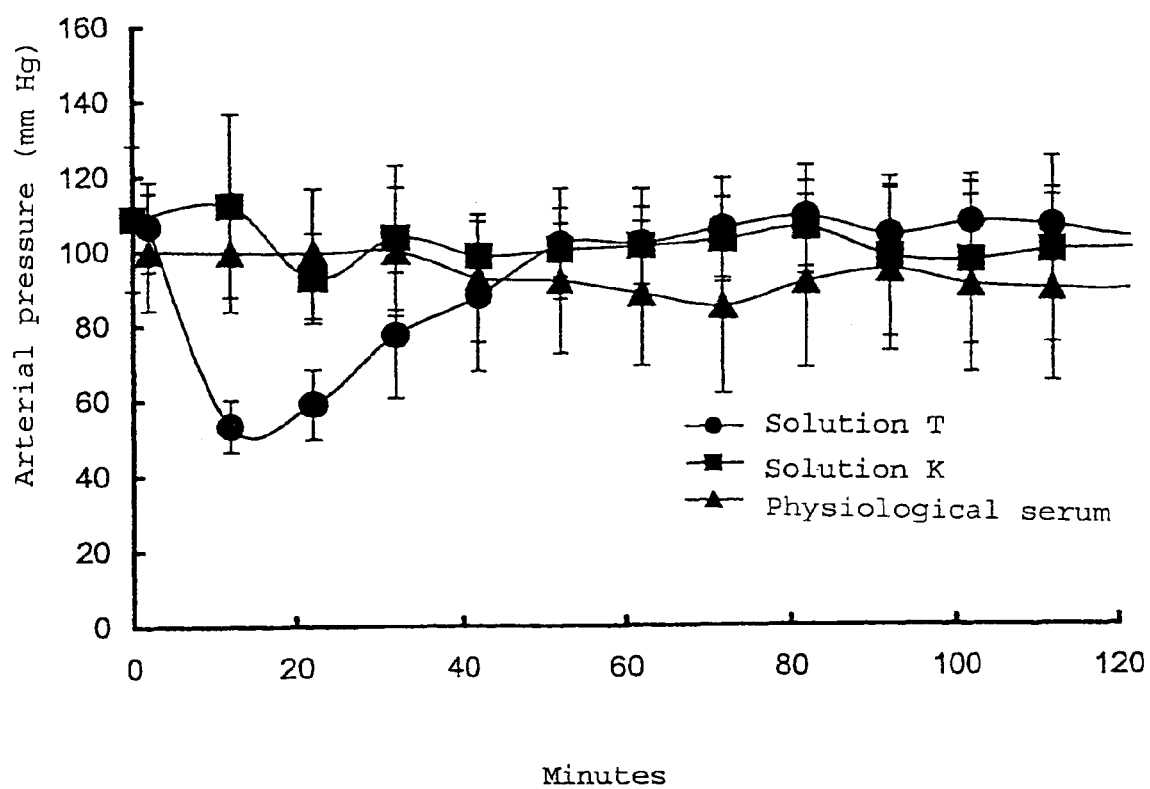

US 8,388,954 B2

STABILISING FORMULATION FOR IMMUNOGLOBULIN G COMPOSITIONS IN LIQUID FORM AND IN LYOPHILISED FORM

FIELD OF THE INVENTION

The present invention is related to a pharmaceutically acceptable stabilising formulation for the stabilization and preservation of immunoglobulins G compositions (IgG), either in liquid form or in lyophilised form.

BACKGROUND OF THE INVENTION

A great number of diseases, for example of auto-immune origin, are treated at present by IgG concentrates and this generated a shortage of IgGs in Europe and in the United-States of America in the last years.

Effectively, there is a growing need for IgG concentrates produced for example from human plasma, which are usually formulated at acidic pH and applicable by intravenous administration. With growing needs for IgGs, the stabilization of intravenously administrable IgG concentrates (IgGIV), intended to be used in therapy, and to be preserved either in liquid form or in lyophilised form, takes on an essential character.

In this respect, it is known that the IgGIVs have to be stabilized, especially in order to avoid the formation of aggregates (oligomers and polymers) capable of activating the complement system, which is associated with the risk of anaphylactic reactions. Furthermore, the presence of dimers in the IgGIVs is correlated with arterial pressure drops in vivo (Bleeker W. K. et al, Blood, 95, 2000. p. 1856-1861). Further physico-chemical deteriorations can also interfere during the storage of IgGs such as, inter alia, oxidation and hydrolysis.

The stabilization of lyophilised or liquid forms of IgGs requires the addition of compounds, selected classically among sugars and aminoacids, in order not only to obtain undenaturated IgG compositions suitable for therapeutical use, but also IgG compositions with an increased storage stability.

The stabilization of lyophilised forms of protein compositions, and especially of IgGs, by addition of specific stabilisers, was investigated in numerous studies. Those cited in scientific papers by M. Pikal, "Freeze-Drying of Proteins, Part 2: Formulation Selection", Biopharm, 3(9); pp. 26-30 (1990) and by Arakawa et al, Pharm. Res., 1991, 8(3), p. 285-291, demonstrate that the addition of a excipient to protein compositions before lyophilisation, increases the stability during the lyophilisation and/or the stability of the lyophilised product during the storage. Some of these stabilisers, however, are known to be precipitating agents of proteins higher than about 100 kDa. Thus, the use of polyethylene glycol (PEG) 3000-6000 is redhibitory in the freezing phase leading to the lyophilisation of the corresponding protein compositions. Osterberg et al, (Pharm. Res., 1997, 14 (7), p. 892-898) has shown the efficiency of a mixture comprising histidine, sucrose, a non-ionic surface active agent and sodium chloride, for the stabilization of lyophilised forms of recombinant factor VIII, and no improvement of its stability was observed through addition of PEG. Moreover, Guo et al, (Biomacromol., 2002, 3(4), p. 846-849) pointed out, that the lyophilisation of horseradish peroxidase in the presence of PEG does not allow to maintain its native structure. Thus, it appears that the presence of PEG is undesirable.

Lyophilised IgGIV compositions are commercially available for example under the trade marks Polygam™ (American Red Cross), Gammar IV™ (Armour Pharmaceutical Company) and Venoglobulin™ I (Alpha), comprising as stabilisers respectively 2% of glucose, 5% of sucrose and 2% of D-mannitol.

The international patent application WO 97/04801 discloses the effect of stabilization of lyophilised monoclonal antibodies formulations (immunoglobulins of G and E type) comprising specific excipients. From these excipients, the combination of glycine/mannitol was not selected because of lack of efficiency compared with other combinations, such as sucrose/glycine and sucrose/mannitol.

However, it is noted that stabilizers suitable for lyophilised forms of IgGIV could be inefficient for liquid IgGIV compositions.

Thus, commercially available liquid IgGIV compositions comprise specific stabilisers, different from those used in the corresponding lyophilised form. For example, the liquid IgGIV compositions comprising as stabilisers 10% maltose, glycine from 0.16 to 0.24 M and 5% D-sorbitol, are respectively known under the trade marks Gamimune N™, Gamimune N™ 10% (Miles Inc.) and Venoglobulin™ (Alpha).

The different nature of the components used for stabilising, IgG compositions in liquid form and in lyophilised form, incited some authors to investigate identical stabilisers or mixtures of stabilisers allowing to preserve the IgG compositions in both forms. In this respect, recent studies were directed to the stabilization of liquid IgGIV compositions Vigam-S and Vigam Liquid (trademarks of the National Blood Authority, England), and after being lyophilised (Vigam-S), comprising an identical mixture of stabilizers, namely albumin and sucrose (K. Chidwick et al, Vox Sanguinis, 77, 204-209, 1999). The solution Vigam Liquid is however formulated at an acidic pH (pH 5), which is a drawback because of the hydrolysis of sucrose into reducing sugars (fructose and glucose) which condense with amino residues of the lysine of IgG and of albumine, giving an instable Schiff's base evolving into Maillard products (browning of the solution). It is understood that the use of excipients which evolve during the preservation of IgGs is not satisfactory, because it is not possible to control the once onset reaction.

Moreover, some previously cited stabilisers, such as maltose or sucrose, cannot be used without risk in individuals suffering from renal failure and/or from diabetes.

In order to overcome the above cited drawbacks, the Applicant put in practice a unique pharmaceutically acceptable stabilising formulation, fulfilling the purpose of stabilization of both considered preservation forms of IgG and to preserve, even to improve, the therapeutical efficiency of these IgGs.

Such a stabilising formulation has especially the advantage of carrying out only one formulation, which facilitates the control of the starting materials, and brings with reduced manufacturing costs combined with the simplification of production flow sheets.

SUMMARY OF THE INVENTION

For that purpose, based upon the observation that sugars and aminoacids are used as stabilisers, the Applicant has demonstrated on the basis preliminary experiments, that some of these stabilisers endowed the liquid IgG compositions with protecting properties against denaturation induced by heat and stirring, but with variable results with respect to the nature of the selected sugar and aminoacid, and that furthermore the stabilising effect of a mixture, for example of two components, could not be deduced from the stabilising effect obtained with each individual component taken alone. Furthermore, some of the tested sugars were not stable at acidic pH values corresponding to the optimal conditioning medium of the liquid IgG compositions.

On the other hand, the stabilisers selected after preliminary tests did not allow to minimise the instability of liquid IgG compositions against the induced oxidation. Then, the Applicant has added a non-ionic detergent, such as Tween®80 or Triton® X 100 and the obtained results were satisfactory.

Consequently, the invention is related to a stabilising formulation for immunoglobulins G compositions, characterized in that the formulation includes a sugar alcohol, glycine and a non-ionic detergent, in order to be suitable for the stabilization of immunoglobulins G compositions in liquid form and in lyophilised form.

DETAILED DESCRIPTION OF THE PREFERRED EMBODIMENTS

The stabilising formulation according to the invention can include, beside a sugar alcohol, glycine and a non-ionic detergent, at least one other additive. This additive can be a compound selected from the different categories of stabilisers classically used in the technical field of the invention, such as surface active agents, sugars and aminoacids, and a as well excipient added to the formulation in order to adjust, for example, the pH, the ionic strength, etc.

Preferably, the formulation according to the invention is consisting of the said sugar alcohol, glycine and non-ionic detergent. Such a stabilising formulation comprising solely these three compounds of the invention, has the advantage to provide a joint stabilization of lyophilised and non lyophilised IgG compositions, and to reduce the length and the costs of manufacturing at industrial scale, owing to the presence of an efficient minimal number of stabilisers.

In the scope of the invention, the liquid IgG compositions are just as well aqueous solutions of polyclonal IgG concentrates, directly obtained by fractionation of human plasma, as those reconstituted in suitable aqueous medium after the lyophilisation of the former. The aqueous medium for the reconstitution is water for injection which can comprise pharmaceutically acceptable excipients and compatible with the IgGs. These IgG compositions can be further subjected to specific virus inactivation/elimination steps. Preferably, the plasma fractionation methods are those described by Cohn et al (J. Am. Chem. Soc. 68, 459, 1946), Kistler et al. (Vox Sang., 7, 1962, 414-424), Steinbuch and al (Rev. Franç. Et. Clin. and Biol., XIV, 1054, 1969) and in the patent application WO 94/9334.

Among the considered sugars, the Applicant selected sugar alcohols on the basis of stability criteria at acidic pH of the conditioning of IgG compositions, thus avoiding the onset of Maillard reactions with immunoglobulins G, of pharmaceutical compatibility and of criteria related to their stabilising action exclusively on either liquid or lyophilised IgG compositions. Indeed, it was noted that a given sugar alcohol used as only stabiliser could correspond only to a liquid form.

Among the sugar alcohols, those preferably used according to the invention are mannitol, sorbitol or isomers thereof, and, more preferably, mannitol.

The glycine, present in the stabilising formulations of the invention, is known to be suitable for the stabilization of IgG compositions but only in liquid form.

The addition of a non-ionic detergent has surprisingly improved, by synergy, the protecting effect of the formulation. Suitable non-ionic detergents are advantageously selected from the group consisting of Tween®80 (polyoxyethylenesorbitan-monooleat), Tween®20 (polyoxyethylenesorbitan-monolaurat), Triton® X 100 (octoxinol 10) and Pluronic®F68 (polyethylenepolypropylene glycols). Tween®80 and Triton® X100 were preferably used.

The concentrations of these compounds will be selected by one of ordinary skill in the art in such a manner as to obtain the desired stabilising effect on the lyophilised and non-lyophilised IgG compositions.

Preferably, the mannitol concentrations are between 30 g/l and 50 g/l, those of detergent between 20 and 50 ppm, and those of the glycine between 7 g/l and 10 g/l.

The invention is also related to IgG compositions in liquid form and/or lyophilised form comprising the stabilising formulation of the invention, which are furthermore usable for therapy and especially for intravenous administration. These IgG compositions in liquid form and/or lyophilised form, owing to the presence of the stabilising formulation of the invention, contain dimers in an amount less than 7% after a storage period of 24 months at 4° C. It is noted, that the storage of the IgG compositions in liquid form during 6 months at room temperature generates an amount of polymers well below the standards set in the European Pharmacopeia (3%), that is to say less than about 0.3%. The IgG compositions in lyophilised form comprise a proportion of polymer about 10 times lower than the tolerated amount after a storage for 12 months at room temperature or for 6 months at 40° C.

Further, the invention is related to the use of a stabilising formulation according to the invention for the stabilization of immunoglobulins G compositions in liquid form obtained directly by the fractioning of human plasma, in lyophilised form and those after reconstitution of the lyophilised forms in a suitable aqueous medium.

The following examples illustrate the invention without however limiting the scope, with reference to FIG. 1 which illustrates graphically the curse of arterial pressure variations in rats depending upon the time, after the injection of different above mentioned immunoglobulin G compositions.

Example 1

Elaboration of the Stabilising Formulation

A concentrate obtained following the method developed by the Applicant in the international patent application WO 02/092632 was used as IgG composition. This concentrate, comprising about 50 g/l of IgG, is adjusted to a pH value of between 4.6 and 4.8 and is subjected to a thermal treatment for 2 hours at 56° C., in order to eliminate the thermolabile impurities.

Mannitol, glycine and Tween®80 or Triton® X100 are added alone or in mixture (test solutions) to this IgG concentrate in concentrations specified in Table 1.

TABLE 1

CHARACTERISTICS OF THE TEST SOLUTIONS

| Test solution | Mannitol (50 g/l) | Glycine (10 g/l) | Detergent (50 ppm) |
|---|---|---|---|
| A (control) | 0 | 0 | 0 |
| B | 1 | 0 | 0 |
| C | 0 | 1 | 0 |
| D | 1 | 1 | 0 |
| E | 0 | 0 | 1 (Triton ® X100) |
| F | 0 | 0 | 1 (Tween ® 80) |
| G | 1 | 0 | 1 (Triton ® X100) |
| H | 1 | 0 | 1 (Tween ® 80) |

TABLE 1-continued

CHARACTERISTICS OF THE TEST SOLUTIONS

| Test solution | Mannitol (50 g/l) | Glycine (10 g/l) | Detergent (50 ppm) |
|---|---|---|---|
| I | 1 | 1 | 1 (Triton ® X100) |
| J | 1 | 1 | 1 (Tween ® 80) |

0: absence of the considered compound
1: presence of the considered compound

Further, the test solutions are subjected to different tests of thermal stress, of stirring stress and of oxidation stress in order to determine their degree of denaturation, by observing the possible presence of residues (particles, aggregates).

The thermal stress is carried out following the paper of P. Fernandes et al, Vox Sanguinis, 1980, 39. p. 101-112. In short, samples of 5 ml of test solution are introduced into crimped glass vials of 10 ml and are then heated in a water bath at 57° C. for 4 hours. The influence of heating on the test solutions is determined by measuring the difference of turbidity after and before the thermal stress. The more the measured turbidity values are low, the more the IgG solutions are stable with regard to the applied thermal stress.

The tests of stirring stress are carried out as described in the paper by H. Levine et al, Journal of Parental Science & technology, 1991, vol. 45, no 3, p. 160-165. Following, the samples of 5 ml of the test solution are introduced into crimped glass tubes of 10 ml protected against light, then each tube is placed in lying position on a mixer IKA Vibrax VXR (from Fisher Scientific, France), and then stirred at 150 rpm for 18 hours at room temperature. The results of stirring stress are determined by comparison of the visual aspects of the test solutions before and after application of the stress. For that purpose, a value scale of the following arbitrary values is defined 0.25: clear solution with one or two suspended particles;
0.50: clear solution with a few fine suspended particles;
0.75: clear solution with a few more suspended particles than those for 0.50;
2.0: slightly modified visual aspect with more suspended particles;
5.0: numerous suspended filaments or particles;
10.0: bigger particles and aggregates, even coagulates.

The oxidation stress is carried out on samples of 5 ml of test solution placed in glass vials of 10 ml. The surface of the liquid is put into the presence of an oxygen-rich atmosphere ($O_2$>21%) for 3 to 4 s. After sealing and stirring, the vials are cooled to a temperature of 5° C. for 15 minutes. The results are determined by comparison of the visual aspects of the test solutions before and after application of the oxidation stress. The results can be expressed numerically according to a scale of values same as that defined for the stirring stress.

Different measuring results obtained after applying the different above stresses, are resumed in Table 2.

TABLE 2

| Test solution | Turbidity (NTU*) | Before stress | After stirring stress | After oxidation stress |
|---|---|---|---|---|
| A | 0.73 | 0.5 | 5.0 | 2.0 |
| B | 0.21 | 0.5 | 3.5 | 2.0 |
| C | 0.63 | 0.5 | 0.5 | 3.5 |
| D | 0.42 | 0.25 | 10.0 | 2.0 |
| E | 0.84 | 0.5 | 1.25 | 1.25 |
| F | 0.36 | 0.5 | 1.25 | 2.0 |
| G | 0.45 | 0.25 | 0.75 | 0.5 |
| H | 0.16 | 0.25 | 0.5 | 1.25 |
| I | 0.41 | 0.25 | 0.5 | 0.75 |
| J | 0.39 | 0.25 | 0.5 | 1.25 |

*NTU: Normalized Turbidity Units

The obtained results show first of all that the addition of only one stabiliser to a solution of IgG concentrate (solutions B, C, E, F), comparing with the control solution A not including stabiliser, allows to improve the protection against two of the three applied stresses. Besides, the joint presence of mannitol and glycine (solution D) is not desirable, the results of agitation stress are clearly lower than those obtained with mannitol and glycine alone (solutions B or C) or even compared with the control solution A. This result demonstrates the importance of the choice of components for elaboration of the stabilising formulation according to the invention, which cannot be consequently deduced from the stabilising effects of individual components only. On the other hand, tests conducted on the test solutions show that the considered specific stabilising formulations I and J provide a very satisfactory protection against the denaturation due to the three applied stresses comparing with the control solution A not including stabiliser. The test solutions G and H containing the stabilising formulations not according to the invention, give however satisfactory results at this stage as well.

Example 2

In order to determine quantitatively the amount of polymers, and especially dimers, present in test solutions G, H, I and J having been subjected to stirring stress according to Example 1, these are subjected to a size exclusion chromatography following the procedure described in the Method of the European Pharmacopœia (European Pharmacopœia, 4th edition, Chapter "Normal human immunoglobulin for intravenous administration", Method 2.2.29).

Table 3 presents the obtained percentages of dimers and polymers.

TABLE 3

| Test solution | Dimers (%) | Polymers (%) |
|---|---|---|
| G | 5.90 | 3.30 |
| H | 7.11 | 3.37 |
| I | 4.98 | 2.17 |
| J | 3.50 | 1.80 |

The lowest percentages of polymers are obtained with the test solutions I and J. These results confirm that the specific formulations of the considered stabilisers I and J offer a very satisfactory protection against the denaturation due to applied stirring stress, as described in Example 1.

After, selection of the formula I and J, only the test solution J was selected for the following example, because of the content of a pharmaceutically acceptable non-ionic detergent, namely Tween®80.

Example 3

The solution J in liquid form (named hereafter "liquid IgGs") is subjected to stability tests depending upon the storage period under current temperature conditions (4° C.). Identical tests are carried out for the lyophilised solution J (lyophilisation period of 45±3 h) designated hereafter "lyophilised IgGs". These stability tests are carried out with liquid solutions J reconstituted if need be with water for injection. They consist of the follow-up for a period of time of 24 months of the evolution of four parameters defined hereafter, three of which are determined in reference to methods contained in the European Pharmacopeia (European Pharmacopœia, 4th Edition, Chapter "Normal human immunoglobulin for intravenous administration":

(a) Evolution of the amount of dimers determined by size exclusion chromatography (Method 2.2.29),
(b) Evolution of the anti-complement activity (Method 2.6.17), and
(c) Evolution of the titer of specific antibodies against the hepatitis B virus, anti HBs (Method 2.7.1).

The fourth parameter (d) defines the evolution of the amount of IgG3 by a nephelometric dosage method known to those of ordinary skill in the art, in the presence of specific anti-IgG3 (DADE-Behring: kit anti-IgG3).

The measurements are carried out after a period of storage for 12 months and for 24 months respectively following the preparation of the liquid solution J ($t_0$).

Measurement results obtained for each test are shown in the following Tables and the data are the average values of three tests.

TABLE 4

| | (a) CONTENT OF DIMERS | | |
|---|---|---|---|
| | $t_0$ (%) | $t_{12\,months}$ (%) | $t_{24\,months}$ (%) |
| liquid IgGs | 3.2 ± 0 | 5.0 ± 1.0 | 5.5 ± 1.1 |
| lyophilised IgGs | 3.2 ± 0 | 3.5 ± 0.7 | 5.0 ± 1.0 |

The increase of the amount of dimers during the storage period falls within the limits of exactitude of the tests and is not sufficiently significant to be able to observe a quantitative denaturation of the compositions.

TABLE 5

| | (b) ANTI-COMPLEMENT ACTIVITY | | |
|---|---|---|---|
| | $t_0$ (%) | $t_{12\,months}$ (%) | $t_{24\,months}$ (%) |
| liquid IgGs | 35 ± 0 | 30 ± 6 | 28 ± 5 |
| lyophilised IgGs | 31 ± 0 | 31 ± 4 | 31 ± 7 |

A slight decrease in the anti-complement activity is observed for the liquid IgG compositions, whereas no evolution is noted in the lyophilized IgGs. This diminution has no clinical significance, solely an increase of this activity would be unfavourable in terms of utilisation.

TABLE 6

| | (c) DETERMINATION OF ANTI HBs | | |
|---|---|---|---|
| | $t_0$ (IU/ml) | $t_{12\,months}$ (IU/ml) | $t_{24\,months}$ (IU/ml) |
| liquid IgGs | 12.0 ± 0 | 11.5 ± 2.5 | 11.0 ± 2.0 |
| lyophilised IgGs | 10.0 ± 0 | 10.0 ± 2.2 | 10.5 ± 2.4 |

Although a very slight decrease seems to take place in the liquid IgGs composition, no significant variation is noted especially for the lyophilised IgG.

TABLE 7

| | (D) IGG3 CONTENT | | |
|---|---|---|---|
| | $t_0$ (g/l) | $t_{12\,months}$ (g/l) | $t_{24\,months}$ (g/l) |
| liquid IgGs | 1.1 | 1.0 ± 0.2 | 1.1 ± 0.1 |
| lyophilised IgGs | 1.1 | 0.9 ± 0.1 | 1.1 ± 0.1 |

The observed variations fall within the uncertainty margin of the values of IgG3 amounts. Therefore, they are not significant.

The four above mentioned parameters demonstrate that the formulation of the invention is particularly suitable for stabilising IgG compositions either in liquid or in lyophilised forms, for a storage period of 24 months at a temperature of 4° C., without noteworthy evolution of these compositions, which would denote, in the opposite case, a denaturation of the product and would thus not be allowed for clinical uses.

Example 4

The composition defined in Example 1 is used as IgG composition. Mannitol, glycine and Tween®80 are added to this IgG concentrate with respective concentrations of 32 g/l, 7 g/l and 50 ppm. The thus obtained solution K in liquid form (designated hereafter "liquid IgGs") is subjected to stability tests depending upon the storage period at 4° C., at room temperature and at 40° C. Identical tests are carried out for the lyophilised solution K (lyophilisation period of 45±3 h), designated hereafter "lyophilised IgGs". These stability tests are carried out with liquid solutions K, reconstituted if need be in water for preparations for injection. The tests consist of the follow-up, for a period of time of 12 months, of the evolution of polymers content determined by size exclusion chromatography with reference to the Method 2.2.29 contained in the European Pharmacopeia, specified in Example 3. The maximal tolerated threshold, defined by the standards of the European Pharmacopeia, is of 3%.

The measurements are carried out respectively after a storage period of 3, 6 and 12 months following the preparation of the liquid solution K ($t_0$).

Measurement results obtained for each test at the three above mentioned storage temperatures are shown respectively in the following Tables 8, 9 and 10, and the given values are average values of three tests.

TABLE 8

| | T: 4° C. | | | |
|---|---|---|---|---|
| | $t_0$ (%) | $t_{3\,months}$ (%) | $t_{6\,months}$ (%) | $t_{12\,months}$ (%) |
| liquid IgGs | 0.057 ± 0.003 | 0.02 ± 0.005 | 0.2 ± 0.03 | — |
| lyophilised IgGs | 0.23 ± 0.05 | 0.2 ± 0.08 | 0.23 ± 0.09 | 0.18 ± 0.07 |

TABLE 9

| | T: room temperature | | | |
|---|---|---|---|---|
| | $t_0$ (%) | $t_{3\,months}$ (%) | $t_{6\,months}$ (%) | $t_{12\,months}$ (%) |
| liquid IgGs | 0.057 ± 0.003 | 0.02 ± 0.01 | 0.19 ± 0.03 | — |
| lyophilised IgGs | 0.23 ± 0.05 | 0.24 ± 0.08 | 0.20 ± 0.1 | 0.20 ± 0.01 |

TABLE 10

| | $t_0$ (%) | $t_{3\,months}$ (%) | $t_{6\,months}$ (%) | $t_{12\,months}$ (%) |
|---|---|---|---|---|
| T: 40° C. | | | | |
| liquid IgGs | 0.057 ± 0.003 | 1.20 ± 0.08 | 6.23 ± 0.03 | — |
| lyophilised IgGs | 0.47 ± 0.3 | 0.55 ± 0.1 | 0.20 ± 0.1 | — |

The storage period of liquid IgGs is of 3 months at 40° C. At the end of a 6 months storage period at 4° C. and at room temperature, the observed content of polymers is well below the standards set by the European Pharmacopœia. For lyophilised IgGs, the storage period of 12 months at 4° C. and at room temperature generates a polymer content which is 10 times lower than the tolerated. The same content is observed after a 6 months storage period at 40° C.

Example 5

This example is intended to confirm that the solutions of the invention, having a dimer content lower than 7%, do not induce hypotensor effects after injection in vivo. Bleeker W. K. et al (Blood, 95, 2000, p. 1856-1861) reports that the more the content of immunoglobulins G dimers in an IgG sample to be injected is high, the more the hypotensor effects in vivo are high. The treatment of auto-immune diseases requires injection of massive doses of IgGs, and can therefore be a risk for patients suffering from hypotension if the dimer content in IgGs is not controlled.

These studies, shown in this example, were aiming to assess and to compare the hemodynamic effects of the two IgG solutions in liquid forms, being respectively a classical IgG solution (Solution T—IgG: 50 g/l; sucrose: 100 g/l; NaCl: 3 g/l, pH: 6.5) containing an amount of dimers of 11.50%, and the solution K from the preceding example containing an amount of dimers of 6.3%, in anaesthetized prepared rats.

Procedure

Adult male Sprague-Dawley (IFFA-Credo: France) rats of 180-200 g are anaesthetized by intraperitoneal injection of pentobarbital (Sanofi—France) at the rate of 60 mg/kg. The anesthesised rat is lied down on the back on a mattress thermostatised at 37° C. A catheter is introduced into the carotide connected with classical pressure sensor and recorder enabling to measure continuously the arterial pressure. A tracheal canule permits to free the respiratory ways. Intravenous administration of IgGs (solutions K and T) is carried out via a catheter introduced into the vena jugularis of the animal at a rate of 2.66 ml/120 min.

Arterial pressure (mm Hg) variations are measured, depending upon the time, on three groups of 6 rats each
 one control group receiving the physiological serum,
 one treated group receiving the solution T at a rate of 0.65 g/kg, and
 one treated group receiving the solution K at a rate of 0.65 g/kg.

The experiments are beginning with a preliminary stabilization phase for 20 min. Continuous recording of the arterial pressure begins at $t_0$−10 min. ($t_0$=injection).

Results of theses studies are read on a chart on the FIG. 1, where each point is the average value, with the standard deviation, of 6 experiments. The statistical analysis is carried out by variance analysis followed by a Scheffé test known by those skilled in the art.

These results demonstrate that the arterial pressure data, before the injection of IgGs, are stable and comparable in the three groups of rats. A diminution of the arterial pressure is noted at $t_0$+10 min, the minimum is reached at about $t_0$+15 min with a value less than 50% of the initial value before injection (sinking from about 100 mm Hg to about 50 mm Hg), followed by a progressive return to the arterial pressure reached at from 50 to 60 minutes after the beginning of the injection.

Example 6

This example is intended to verify whether the solution J in liquid form contributes to the reduction of blood viscosity comparing with solutions comprising proteins and different excipients. For that purpose, two gravity sedimentation tests of red blood cells were carried out by means of methods known of those skilled in the art, at room temperature and at T=37° C.

Procedure

Human red blood cells of the group 0+ in the presence of an anticoagulant solution of trisodium citrate 0.2 M (1/9, v/v) are washed three times with a saline solution of PBS in usual concentration, pH 7.4. Aqueous solutions of proteins in various excipients are prepared, of which the solution J is adjusted to NaCl 0.15 M and pH 7. The proteins and excipients, and their respective concentrations as well, are shown in Table 11. Samples of 4.5 ml of each protein solutions are taken and introduced into a calibrated glass tube of 10 ml. 0.5 ml of washed red blood cells are then added to each solution. Obtained mixtures are homogenised by turning the sealed tubes 3-4 times upside down. At the end of homogenisation, the tubes are left to rest on a counter display and the time necessary to the apparition of a charp decantation line of red cells tangent to the clear meniscus, expressing the rate of sedimentation, is measured. The results of experiments at room temperature are shown in Table 11.

TABLE 11

TESTS AT ROOM TEMPERATURE

| Protein(s) | Solution | Sedimentation time at the meniscus (min.) | Remark |
|---|---|---|---|
| — | PBS | 22.70 | Control (no protein) |
| Albumin (5%) | NaCl: 2 g/l | 35.90 | Oncotic protein |
| Human plasma | NaCl: 2 g/l trisodium citrate: 0.02 M | 28.42 | All present proteins |
| IgG (50 g/l) | Sucrose: 100 g/l NaCl: 3 g/l | 31.25 | Formulation of the prior art |
| Solution J | +NaCl: 0.15 M | 9.25 | Formulation of the invention |
| Fibrinogen (15 g/l) | Arginine: 40 g/l trisodium citrate: 2.5 g/l lysine: 2 g/l | 12.60 | Presence of agglutinates |

Obtained results show that the considered red blood cells, in the presence of IgGs of the solution J of the invention, have a higher sedimentation rate which corresponds to a diminution of the viscosity of the examined mixture, thus enabling to obtain a better blood fluidity.

Further tests were carried out with the above mixtures (4.5 ml of protein solutions and 0.5 ml of washed red blood cells) introduced into calibrated glass tubes of 10 ml and homogenised by returning the tubes 3-4 times upside down. As soon as this operation is accomplished, the tubes are placed in such a manner that their content be sedimented within 1 hour under a 45° angle, at a temperature of 37° C., and the supernatant volume of the examined mixtures is measured. Test results at T=37° C. are shown in Table 12.

TABLE 12

TESTS AT T = 37° C.

| Protein(s) | Solution | Supernatant volume after 1 hour (ml) |
|---|---|---|
| — | PBS | 2.5 |
| Albumin (5%) | NaCl: 2 g/l | 2.5 |
| Human plasma | NaCl: 2 g/l trisodium citrate: 0.02 M | 4 |
| IgG (50 g/l) | Sucrose: 100 g/l NaCl: 3 g/l | 1* |
| Solution J | +NaCl: 0.15 M | 2.5 |

*supernatant showing signs of hemolysis

The analysis of the results in Table 12 shows that:
the supernatant volume of the plasma mixture is the highest among the examined mixtures, showing therefore the corresponding lowest viscosity;
the mixtures of albumin and of solution J of the invention show an identical sedimentation rate (same volume of supernatant)
the IgG mixture of the prior art, i.e. comprising sucrose and NaCl, leads to the lowest volume of supernatant, meaning that the sedimentation of red blood cells is slower than in the mixture J of the invention, moreover, as in the other above examined mixtures, as well, the supernatant being rose coloured because of its discrete hemolysis.

The invention claimed is:

1. A stabilizing formulation consisting of mannitol, glycine and a non-ionic detergent, suitable for the stabilisation of an immunoglobulin G composition in liquid form and in lyophilised form, wherein the concentration of mannitol is between 30 g/l and 50 g/l, and wherein the concentration of glycine is between 7 g/l and 10 g/l.

2. An immunoglobulin G composition in liquid form, consisting of immunoglobulins G, water and the stabilising formulation according to claim 1.

3. An immunoglobulin G composition in lyophilised form, consisting of immunoglobulins G and the stabilising formulation according to claim 1.

4. The immunoglobulin G composition according to claim 2, wherein the composition includes an amount of polymers less than 0.3% after a 6 months storage period at room temperature.

5. The immunoglobulin G composition according to claim 3, wherein the composition includes an amount of polymers less than 0.3% after a 12 months storage period at room temperature of for 6 months at 40° C.

6. The immunoglobulin G composition according to claim 1, wherein the composition includes an amount of dimers less than 7% after a 24 months storage period at 4° C.

* * * * *

UNITED STATES PATENT AND TRADEMARK OFFICE
CERTIFICATE OF CORRECTION

PATENT NO. : 8,388,954 B2  Page 1 of 1
APPLICATION NO. : 10/552314
DATED : March 5, 2013
INVENTOR(S) : Bardat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 975 days.

Signed and Sealed this
First Day of September, 2015

Michelle K. Lee
*Director of the United States Patent and Trademark Office*